US00PP19065P3

(12) United States Plant Patent
Cain et al.

(10) Patent No.: US PP19,065 P3
(45) Date of Patent: Aug. 5, 2008

(54) GRAPEVINE PLANT NAMED 'SUGRATHIRTYONE'

(50) Latin Name: *Vitis vinifera*
Varietal Denomination: Sugrathirtyone

(75) Inventors: David W. Cain, Bakersfield, CA (US); Michael J. Striem, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 318 days.

(21) Appl. No.: 11/329,195

(22) Filed: Jan. 10, 2006

(65) Prior Publication Data

US 2007/0163017 P1 Jul. 12, 2007

(51) Int. Cl.
*A01H 5/00* (2006.01)

(52) U.S. Cl. ..... Plt./205

(58) Field of Classification Search ..... Plt./205
See application file for complete search history.

(56) References Cited

U.S. PATENT DOCUMENTS

PP3,106 P * 4/1972 Garabedian

* cited by examiner

*Primary Examiner*—Anne Marie Grunberg
*Assistant Examiner*—Georgia Helmer
(74) *Attorney, Agent, or Firm*—Knobbe Martens Olson & Bear LLP

(57) ABSTRACT

A new and distinct grapevine variety characterized by possessing elliptic shaped, medium sized green-yellowish seedless grapes having a crisp flesh texture. The grapes have a mild neutral flavor, medium sugar content, and excellent eating quality. The new variety possesses exceptional late-ripening characteristics. Additionally, the bunches have the ability to stay on the vine for a month or more, while maintaining commercial harvest quality.

1 Drawing Sheet

Latin name of the genus and species claimed: *Vitis vinifera.*
Variety denomination: 'Sugrathirtyone'.

BACKGROUND AND SUMMARY OF THE INVENTION

This invention relates to the discovery and asexual propagation of a new variety of grapevine as herein described and illustrated. The new variety was first hybridized by David. W. Cain and Michael J. Striem in Wasco, Kern County, Calif., the variety being originated by controlled hybridization and subsequent culture of seed traces and embryo rescue procedures.

The new variety 'Sugrathirtyone' is characterized by possessing medium sized green-yellowish seedless grapes having a mild neutral flavor. The grapes have an elliptic shape, a crisp flesh texture, medium sugar content and excellent eating quality. The new variety 'Sugrathirtyone' is exceptional with its late ripening, as the grapes ripen after any other seedless grape cultivars grown and marketed commercially in California. Further, the bunches are able to stay on the vine for a month or more, while still maintaining commercial harvest quality.

The new variety 'Sugrathirtyone' was created by hybridization of two "seedless" grapes possessing small, abortive, vestigial ovules. From the initial population of hybrid ovules, embryo rescue methods were used to produce a population from which the present variety was selected. The seed parent is '92147-050-238' (unpatented) and the pollen parent is '92187-055-030' (unpatented). The parent varieties were first crossed in May 1999, with the date of first sowing being August 1999, and the date first flowering being May 2001.

The new 'Sugrathirtyone' variety was first asexually propagated by Dr. Michael Striem in December 2001 in Wasco, Kern County, Calif. using hardwood cuttings.

The new variety 'Sugrathirtyone' resembles its seed parent '92147-050-238' in berry color and shape. However, 'Sugrathirtyone' has a much larger natural berry size of approximately 4.55 grams, compared to the seed parent's natural berry size of approximately 3.35 grams. Additionally, the seed parent has a noticeable, dark and hard seed-trace while the seed-trace of 'Sugrathirtyone' is very small and soft.

The new variety 'Sugrathirtyone' resembles its pollen parent '92187-055-030' in berry color and shape. However, 'Sugrathirtyone' has a much larger natural berry size of 4.55 grams, compared to the pollen parent's natural berry size of 4.26 grams. Further, while the berries of the pollen parent turn brown when exposed to direct sunshine, the berries of the new variety 'Sugrathirtyone' stay light-green with a milky-creamy/opaque look, turning slightly yellowish at the end of the harvest season.

The new variety 'Sugrathirtyone' is similar to the comparable variety 'Sugraone' (U.S. Pat. No. 3,106) in its appearance, bunch structure and berry shape. However, the new variety ripens about 6–8 weeks later than 'Sugraone.' The new variety 'Sugrathirtyone' also develops higher sugar levels than 'Sugraone' at harvest.

It is to be understood that variations of the usual magnitude from the described above may occur with changes in growing conditions, irrigation, fertilization, pruning, management and climatic variations.

The new 'Sugrathirtyone' variety has been shown to maintain its distinguishing characteristics through successive asexual propagations by, for example, cuttings.

BRIEF DESCRIPTION OF THE FIGURE

The accompanying drawing in FIG. 1 illustrates in full color a typical cluster of berries, a young shoot, and a mature leaf blade of the new grapevine at 5 years of age. The colors are as nearly true as is reasonably possible in a color representation of this type.

DETAILED BOTANICAL DESCRIPTION OF THE INVENTION

Figure 1:
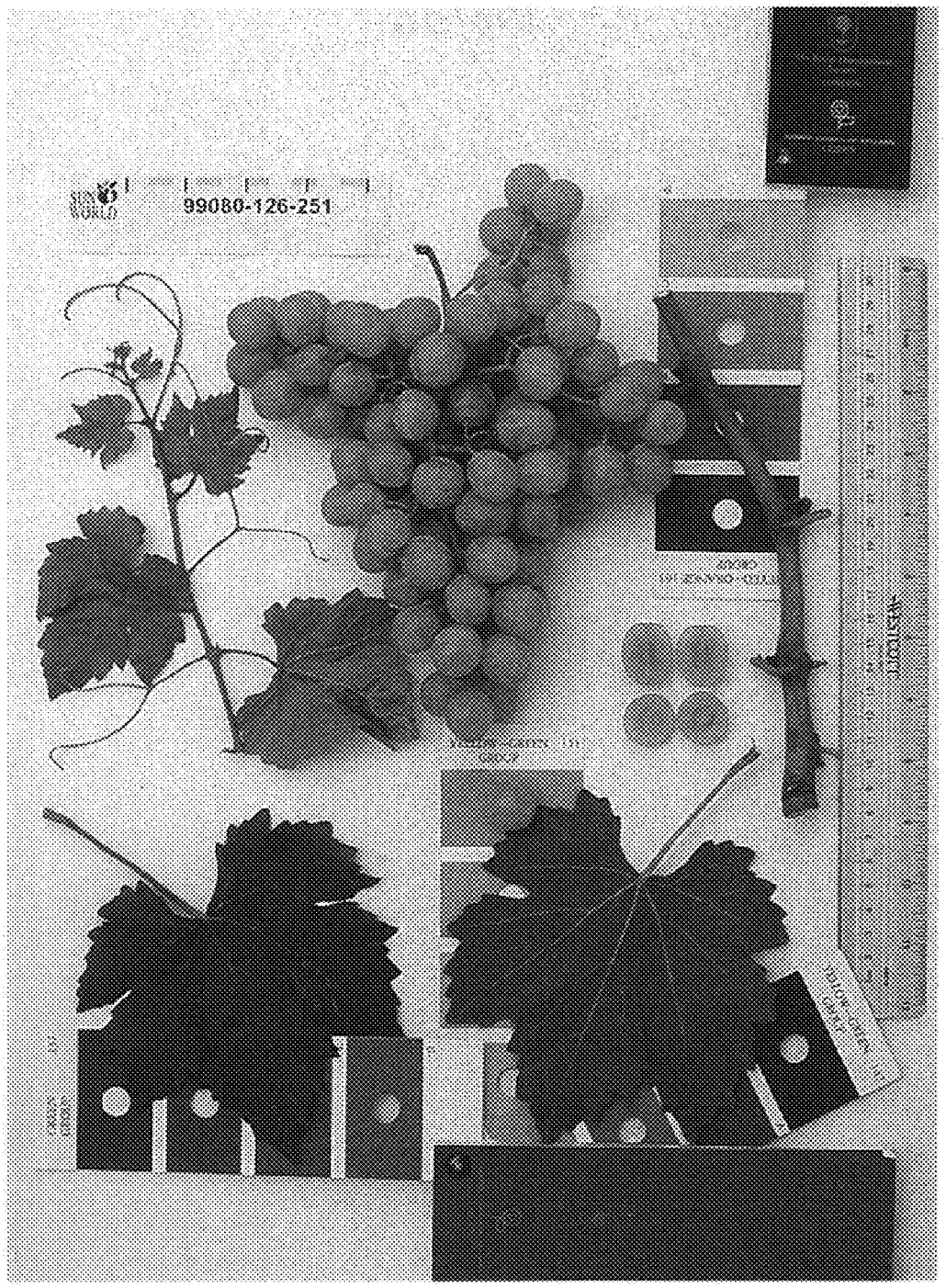

Throughout this specification, color names beginning with a small letter signify that the name of that color, as used in common speech, is aptly descriptive. Color names beginning with a capital letter designate values based upon the R.H.S. Colour Chart, published by The Royal Horticultural Society, London, England.

Many of the description values in this specification are based on and conform to those set forth by the International Board for Plant Genetic Resources Institute Grape Descriptors (Vitis spp.) of 1983 and/or 1997 which was developed in collaboration with the Office International de la Vigne et du Vin (OIV) and the International Union for the Protection of New Varieties of Plants (UPOV).

The descriptive matter which follows pertains to 'Sugrathirtyone' plants grown in the vicinity of Wasco, Kern County, Calif., during 2002, 2003, and 2004, and is believed to apply to plants of the variety grown under similar conditions of soil and climate elsewhere:

VINE

General:

*Planting.*—Trained on 'Cross-Arm'/T trellis, planted in a 7 ft.×12 ft. spacing.

*Practices.*—Gene-pool-vine: Cane pruned to approximately 6 canes per vine and trimmed once in the early summer. Test-vines: Spur pruned to approximately 12 to 18 two-bud-spurs per vine.

*Size.*—Medium. Height: Approximately 1.80 to 2.10 m. Width: Approximately 1.70 to 2.00 m.

*Vigor.*—Medium-weak.

*Fresh pruning weight.*—Approximately 1.9 kg per vine.

*Density of foliage.*—Medium.

*Productivity.*—Very productive — approximately 95 clusters per vine.

*Yield.*—Approximately 11.73 kg per vine, thinned to approximately 32 clusters per vine.

*Crop load.*—Approximately 6.17 kg per vine (kg fruit per kg fresh-pruning-weight).

*Root stock.*—Not applicable.

*Own root.*—Yes.

Trunk:

*Cross section shape.*—Irregular flat elliptic to broadly elliptic.

*Diameter (at 20 cm above soil level).—Approximately* 52 mm.

*Straps.*—Split.

*Surface texture.*—Shaggy.

*Inner back color.*—Near Greyed-orange 177A.

*Outer bark color.*—Near Brown 200A with near Grey 201B.

SHOOTS

Young shoot:

*Form of tip.*—Slightly open.

*Distribution of anthocyanin coloration of tip.*—Absent.

*Intensity of anthocyanin coloration of tip.*—Absent.

*Density of prostrate hairs on tip.*—Very sparse.

*Density of erect hairs on tip.*—Absent.

Woody shoot:

*Shape.*—Slender.

*Internode length.*—Approximately 36.8 mm.

*Width at node.*—Approximately 10.8 mm.

*Cross section.*—Circular.

*Surface.*—Smooth.

*Main color.*—Near Greyed-orange 165B.

*Lenticels.*—Absent.

*Density of erect hairs on nodes.*—None or very sparse.

*Density of erect hairs on internodes.*—None or very sparse.

*Growth of axillary shoots.*—Medium, approximately 21.72 cm.

Flowering shoot:

*Vigor during flowering.*—Weak.

*Attitude during flowering on shoots which are not tied.*—Semi-erect.

*Color of dorsal side of internodes.*—Near Yellow-green 144A with near Greyed-purple 183C stripes.

*Color of ventral side of internodes.*—Near Yellow-green 144A with near Greyed-purple 183C stripes.

*Color of dorsal side of nodes.*—Near Yellow-green 144A near Greyed-purple 183C stripes.

*Color of ventral side of nodes.*—Near Yellow-green 144A with near Greyed-purple 183C stripes.

*Density of erect hairs on nodes.*—None.

*Erect hairs on internode.*—Absent.

*Density of prostrate hairs on nodes.*—None.

*Density of prostrate hairs on internodes.*—Absent.

*Anthocyanin coloration of buds.*—Weak.

Tendrils:

*Distribution of the shoot at full flowering.*—Discontinuous.

*Thickness.*—Medium.

*Color.*—Near Yellow-green 145A.

*Form.*—Bifurcated.

*Number of consecutive tendrils.*—Up to 2.

*Length of tendril.*—Short, approximately 8.24 cm.

LEAVES

Young leaves:

*Color of upper surface of first* 4 *distal unfolded leaves.*—Near Yellow-green 144A.

*Average intensity of anthocyanin coloration of six distal leaves prior to flowering.*—Absent or very weak.

*Density of prostrate hairs between veins at lower surface of* 4*th distal unfolded leaf.*—Absent.

*Density of erect hairs between veins at lower surface of* 4*th distal unfolded leaf.*—Absent.

*Density of prostrate hairs on veins at lower surface of* 4*th distal unfolded leaf.*—Absent.

*Density of erect hairs on veins at lower surface of* 4*th distal unfolded leaf.*—Absent.

Mature leaves:

*Average length.*—Approximately 114.6 mm.

*Average width.*—Approximately 156.6 mm.

*Size of blade.*—Medium.

*Shape of blade.*—Circular.

*Number of lobes.*—Approximately 3.
*Anthocyanin coloration of main veins on the upper side of the blade.*—Absent.
*Mature leaf profile.*—Flat.
*Blistering surface of blade upper surface.*—Absent.
*Leaf blade tip.*—In the plane of the leaf.
*Undulation of margin.*—Slight.
*Thickness.*—Medium.
*Undulation of blade between main and lateral veins.*—Absent.
*Shape of teeth.*—Both sides convex.
*Length of teeth.*—Medium.
*Ratio length/width of teeth.*—Medium.
*General shape of petiole sinus.*—Half open.
*Tooth at petiole sinus.*—Absent.
*Petiole sinus limited by veins.*—Absent.
*Shape of upper lateral sinus.*—Open.
*Depth of upper lateral sinus.*—Very shallow.
*Density of prostrate hairs between veins on lower surface of blade.*—Absent.
*Density of erect hairs between veins on lower surface of blade.*—Absent.
*Density of prostrate hairs on main veins on lower surface of blade.*—Absent.
*Density of erect hairs on main veins on lower surface of blade.*—Absent.
*Density of prostrate hairs on main veins on upper surface of blade.*—Absent.
*Autumn coloration of leaves.*—Near Greyed-yellow 162A. Slow to develop. Normally frost kills leaves before extensive color change.

Upper surface:
*Color.*—Near Green 137A.
*Surface texture.*—Smooth.
*Surface appearance.*—Dull.

Lower surface:
*Color.*—Near Yellow-green 147B.
*Anthocyanin coloration of main veins on lower leaf surface.*—Absent.
*Glossiness.*—Weak.
*Pubescence.*—Absent.
*Surface texture.*—Smooth.
*Surface appearance.*—Dull.

Petiole:
*Length of petiole.*—Medium, approximately 11.22 cm.
*Length of petiole compared to middle vein.*—Slightly shorter.
*Diameter.*—Approximately 3.5 mm.
*Density of prostrate hairs on petiole.*—None.
*Density of erect hairs on petiole.*—None.
*Shape of base of petiole sinus.*—V-shaped.
*Color.*—Near Yellow-green 145B.

Buds:
*Shape.*—Slightly pointed.
*Size.*—Large, approximately 6 mm×7 mm.
*Position.*—Slightly held out, approximately 45° angle.
*Cane bud fruitfulness.*—Basal most fruitful.
*Time of bud burst.*—Medium, Mar. 15, 2004.

FLOWERS

General:
*Flower sex.*—Hermaphrodite.
*Length of first inflorescence.*—Long, approximately 29.5 cm.
*Position of first flowering node.*—Fourth.
*Number of inflorescences per shoot.*—Approximately 1.1 to 2.
*Date of full bloom.*—Approximately May 18, 2004.
*Time of bloom.*—Medium.
*Size (diameter of fully open flower).*—Medium, approximately 5 mm.

FRUIT

General:
*Ripening period.*—Late, approximately 22 days after 'Thompson Seedless' (unpatented) variety.
*Use.*—Fresh market.
*Keeping quality.*—Good.
*Shipping quality.*—Good.
*Date of first harvest.*—Approximately Sep. 5, 2004.
*Solids-sugar.*—Medium (≈18%). Refractometer test: Approximately 18.4. Acid: Medium, approximately 4.24 gr./L tartaric acid.
*Juice pH.*—Approximately 3.7.
*Tendency to crack.*—Absent.
*Sensitivity to sunburn.*—Absent.
*Fruit shrivel after ripe.*—Absent.
*Secondary clusters.*—Many.
*Resistance.*—Neither resistance nor susceptibility to diseases or pests has been observed in this variety.

Cluster:
*Bunch size (peduncle excluded).*—Small.
*Bunch length (peduncle excluded).*—Intermediate, approximately 22.8 cm.
*Bunch width.*—Approximately 11.32 cm.
*Bunch weight.*—Low, approximately 367 g.
*Bunch density.*—Medium.
*Number of berries.*—Approximately 109.2.
*Form.*—Conical.

Peduncle:
*Length of peduncle.*—Medium, approximately 44.78 mm.
*Lignification of peduncle.*—Medium.
*Color.*—Near Yellow-green 144A.

Berry:
*Size.*—Medium.
*Uniformity of size.*—Variable.
*Berry weight.*—Natural: Medium, approximately 4.55 g. Gibberellic acid treated: High, approximately 7.26 to 8.74 g.
*Shape.*—Broad elliptic.
*Presence of seeds.*—Rudimentary.
*Cross section.*—Circular.
*Dimensions.*—Longitudinal axis: Approximately 18.96 mm. Horizontal axis: Approximately 17.14 mm.
*Skin color (without bloom).*—Near Yellow-green 151A.
*Coloration of flesh.*—Near Greyed-yellow 161A.
*Juiciness of flesh.*—Slightly juicy.
*Berry firmness.*—Firm.
*Particular flavor.*—None.
*Bloom (cuticular wax).*—Very weak.
*Pedicel length.*—Intermediate, approximately 7.6 mm.
*Berry separation from pedicel.*—Medium.
*Visibility of hilum.*—Unclear.

Skin:
*Thickness.*—Medium.
*Texture.*—Medium.
*Reticulation.*—Absent.
*Roughness.*—Absent.
*Tenacity.*—Tenacious to flesh.

Seed:

*Number of seeds per berry.*—Approximately 1.1.

*Size.*—Small.

*Color.*—Ranges between green to yellow. Seed color changes dramatically with environmental conditions and maturity.

*Texture.*—Soft.

*Endosperm.*—Absent.

*Fresh weight of seed-traces/berry.*—Approximately 50.6 mg.

*Room-dry weight of seed-traces/berry.*—Approximately 0.48 mg.

What is claimed is:

1. A new and distinct variety of grapevine as herein illustrated and described.

* * * * *